United States Patent
Larson et al.

(10) Patent No.: US 10,650,928 B1
(45) Date of Patent: May 12, 2020

(54) COMPUTER NETWORK ARCHITECTURE FOR A PIPELINE OF MODELS FOR HEALTHCARE OUTCOMES WITH MACHINE LEARNING AND ARTIFICIAL INTELLIGENCE

(71) Applicant: Clarify Health Solutions, Inc., San Francisco, CA (US)

(72) Inventors: Jeffrey D. Larson, San Francisco, CA (US); Yale Wang, San Francisco, CA (US); Samuel H. Bauknight, San Francisco, CA (US)

(73) Assignee: Clarify Health Solutions, Inc., San Francisco, CA (US)

( * ) Notice: Subject to any disclaimer, the term of this patent is extended or adjusted under 35 U.S.C. 154(b) by 0 days.

(21) Appl. No.: 15/845,633

(22) Filed: Dec. 18, 2017

(51) Int. Cl.
*G16H 50/20* (2018.01)
*G16H 15/00* (2018.01)
*G06Q 40/08* (2012.01)
*G16H 10/60* (2018.01)
*G06Q 40/02* (2012.01)
*G06N 20/00* (2019.01)

(52) U.S. Cl.
CPC ............ *G16H 50/20* (2018.01); *G16H 15/00* (2018.01); *G06N 20/00* (2019.01); *G06Q 40/025* (2013.01); *G06Q 40/08* (2013.01); *G16H 10/60* (2018.01)

(58) Field of Classification Search
CPC ......... G16H 50/30; G16H 15/00; G06Q 50/24
See application file for complete search history.

(56) References Cited

U.S. PATENT DOCUMENTS

| | | |
|---|---|---|
| 7,917,377 B2 | 3/2011 | Rao |
| 8,508,336 B2 | 8/2013 | Giobbi |
| 9,002,719 B2 | 4/2015 | Tofte |
| 9,195,732 B2 | 11/2015 | Anderson et al. |
| 10,127,234 B1 | 11/2018 | Krishnan |
| 2005/0038669 A1 | 2/2005 | Sachdeva |
| 2005/0137912 A1 | 6/2005 | Rao |
| 2005/0222867 A1 | 10/2005 | Underwood |
| 2006/0052945 A1 | 3/2006 | Rabinowitz et al. |
| 2006/0080139 A1 | 4/2006 | Mainzer |
| 2006/0178915 A1 | 8/2006 | Chao |
| 2007/0005154 A1 | 1/2007 | Lancaster |
| 2007/0260492 A1 | 11/2007 | Feied |
| 2008/0120133 A1 | 5/2008 | Krishnaswami |
| 2008/0146893 A1 | 6/2008 | Levendoswki |
| 2008/0183508 A1 | 7/2008 | Harker |

(Continued)

OTHER PUBLICATIONS

Wang et al., U.S. Appl. No. 16/007,819, filed Jun. 13, 2018.

(Continued)

*Primary Examiner* — Robert A Sorey
*Assistant Examiner* — Kristine K Rapillo
(74) *Attorney, Agent, or Firm* — Akerman LLP; Stephen C. Glazier

(57) ABSTRACT

A computer network architecture for a pipeline of models with machine learning and artificial intelligence for healthcare outcomes is presented. A machine learning prediction module and an artificial intelligence learning model are in electronic communication with a web application, which is also in electronic communication with a user device. An expanding updating database supports automatically recalibrating, re-evaluating, and reselecting the evolving and improving algorithms.

7 Claims, 7 Drawing Sheets

(56) References Cited

U.S. PATENT DOCUMENTS

| | | |
|---|---|---|
| 2009/0006419 A1 | 1/2009 | Savitsky |
| 2009/0048877 A1 | 2/2009 | Binns |
| 2009/0192828 A1 | 7/2009 | Yunker |
| 2009/0206992 A1 | 8/2009 | Giobbi |
| 2009/0222290 A1 | 9/2009 | Crowe |
| 2011/0112871 A1 | 5/2011 | Simonowski |
| 2011/0166883 A1 | 7/2011 | Palmer |
| 2011/0213625 A1 | 9/2011 | Joao |
| 2011/0270630 A1 | 11/2011 | Green, III |
| 2011/0289035 A1 | 11/2011 | Stojadinovic et al. |
| 2012/0047105 A1 | 2/2012 | Saigal |
| 2012/0179478 A1* | 7/2012 | Ross ............... G06F 19/328 705/2 |
| 2012/0271612 A1* | 10/2012 | Barsoum ............ G06F 19/00 703/11 |
| 2012/0310661 A1 | 12/2012 | Greene |
| 2013/0054259 A1 | 2/2013 | Wojtusiak |
| 2013/0096937 A1 | 4/2013 | Campbell |
| 2013/0159023 A1 | 6/2013 | Srinivas |
| 2013/0197936 A1 | 8/2013 | Willich |
| 2013/0226624 A1 | 8/2013 | Blessman |
| 2013/0290028 A1 | 10/2013 | McGuigan |
| 2013/0290037 A1 | 10/2013 | Hu |
| 2013/0304618 A1 | 11/2013 | Mastrogiovanni |
| 2014/0046682 A1 | 2/2014 | Soto |
| 2014/0058763 A1 | 2/2014 | Zizzamia |
| 2014/0081652 A1 | 3/2014 | Klindworth |
| 2014/0316810 A1 | 10/2014 | Oliver |
| 2015/0088541 A1 | 3/2015 | Yao |
| 2015/0095069 A1* | 4/2015 | Waljee ............... G16H 50/30 705/3 |
| 2015/0100336 A1 | 4/2015 | Ford |
| 2015/0261922 A1 | 9/2015 | Nawana |
| 2015/0302178 A1 | 10/2015 | Patel |
| 2015/0347705 A1 | 12/2015 | Simon |
| 2016/0078578 A1 | 3/2016 | Tumma |
| 2016/0092641 A1 | 3/2016 | Delaney |
| 2016/0196398 A1 | 7/2016 | Vivero |
| 2016/0328526 A1 | 11/2016 | Park |
| 2017/0029894 A1* | 2/2017 | Damask ............ C07K 16/244 |
| 2017/0053080 A1 | 2/2017 | Geppert |
| 2017/0140114 A1 | 5/2017 | Are |
| 2017/0169173 A1 | 6/2017 | Snow, Jr. |
| 2017/0236063 A1 | 8/2017 | Dorris |
| 2017/0249434 A1 | 8/2017 | Brunner |
| 2017/0270257 A1 | 9/2017 | St. Clair |
| 2017/0293722 A1 | 10/2017 | Valverde, Jr. |
| 2017/0308650 A1 | 10/2017 | Brill |
| 2017/0308652 A1 | 10/2017 | Ligon |
| 2017/0308981 A1 | 10/2017 | Razavian |
| 2017/0372028 A1 | 12/2017 | Zhou |
| 2018/0025126 A1 | 1/2018 | Barnard |
| 2018/0060744 A1 | 3/2018 | Achin |
| 2018/0137247 A1 | 5/2018 | Bore |
| 2018/0182475 A1 | 6/2018 | Cossler |
| 2019/0005115 A1 | 1/2019 | Warrier |
| 2019/0005195 A1 | 1/2019 | Peterson |
| 2019/0325995 A1 | 10/2019 | Malone |

OTHER PUBLICATIONS

Drouin et al., U.S. Appl. No. 16/373,316, filed Apr. 2, 2019.
Larson et al., U.S. Appl. No. 15/998,771, filed Aug. 16, 2018.
Gottula et al., U.S. Appl. No. 16/387,713, filed Apr. 18, 2019.
Talvola et al., U.S. Appl. No. 16/404,446, filed May 6, 2019.
U.S. Appl. No. 16/584,326, filed Sep. 26, 2019.
Warner et al.U.S. Appl. No. 16/587780, filed Sep. 30, 2019.
Drouin et al., U.S. Appl. No. 16/533,465, filed Aug. 6, 2019.
Sheth et al., Active Semantic Electronic Medical Records, 5th Int'l Semantic Web Conference, Athens, GA, Nov. 6-Nov. 9, 2006.
Wang et al., U.S. Appl. No. 16/694,292, filed Nov. 25, 2019.
Larson et al., U.S. Appl. No. 16/694,330, filed Nov. 25, 2019.
Talvola et al., U.S. Appl. No. 16/697,773, filed Nov. 27, 2019.
Thesmar et al., "Combining the Power of Artificial Intelligence with the Richness of Healthcare Claims Data: Opportunities and Challenges" Mar. 8, 2019, PharmoEconomics, No. 37, pp. 745-752. (Year: 2019).
Luo et al., "Automating Construction of Machine Learning Models with Clinical Big Data: Proposal Rationale and Methods" Aug. 29, 2017, J MIR Res Protoc, vol. 6, No. 8, pp. 1-18. (Year: 2017).
Bjarnadottir, Margret Vilborg, "Data-Driven Approach to Health Care: Applications Using Claims Data" Sep. 2008, Doctoral Thesis, MIT, pp. i-130. (Year: 2008).
Lix et al., "A Prediction model to estimate completeness of electronic physician claims databases" May 11, 2015, BMJ Open, pp. 1-8. (Year: 2015).
Bertsimas et al., "Algorithmic Prediction of Health-Care Costs" Dec. 2008, Operations Research, vol. 56, No. 6, pp. 1382-1392. (Year: 2008).
Xie et al., "Predicting Days in Hospital Using Health Insurance Claims" Jul. 2015, IEEE Journal of Biomedical and Health Informatics, vol. 19, No. 4, pp. 1224-1233. (Year: 2015).
Hamad et al., "Using 'Big Data' to Capture Overall Health Status: Properties and Predictive Value of a Claims-Based Health Risk Score" May 7, 2015, PLoS One, vol. 10, No. 5, pp. 1-14. (Year: 2015).
Yen et al., "Association Between Wellness Score from a Health Risk Appraisal and Prospective Medical Claims Costs" Oct. 2003, JOEM, vol. 45, No. 10, pp. 1049-1057. (Year: 2003).
Sushmita et al., "Population Cost Prediction on Public Healthcare Datasets" May 18-20, 2015, pp. 87-94. (Year: 2015).
Sears et al., "Predicting work-related disability and medical cost outcomes: A comparison of severity scoring methods" Dec. 28, 2012 , Injury, Int J Care Injured, vol. 45, pp. 16-22. (Year: 2012).
Ramamurthy et al., "A Configurable, Big Data System for On-Demand Healthcare Cost Prediction" 2017, IEEE International Conference on Big Data, pp. 1524-1533. (Year: 2017).
Layton, "Risk Selection and Risk Adjustment in Competitive Health Insurance Markets" 2014, Doctoral Dissertation, Boston University, pp. i-179. (Year: 2014).
Wang, "Competition in the Market of Health Insurance and Health Care Utilization", 2017, Doctoral Dissertation, Boston University, pp. i-123. (Year: 2017).

\* cited by examiner

COMPUTER NETWORK ARCHITECTURE FOR A PIPELINE OF MODELS FOR HEALTHCARE OUTCOMES WITH MACHINE LEARNING AND ARTIFICIAL INTELLIGENCE

TECHNICAL FIELD

The present disclosure is related generally to computer network architectures for machine learning, and more specifically, to computer network architectures for machine learning operations that integrate data analysis techniques to automatically select, improve and operate predictive models.

BACKGROUND

Predictive analysis includes predictive modeling and machine learning. Predictive analysis may be useful to provide predictions of future events or outcomes based on past events, circumstances, known variables, and underlying assumptions. Such predictions may be helpful, for example, to forecast events such as weather, drive times, and operational life of equipment. Predictive analysis is also applied by businesses to predict inventory needs, operational life of equipment, and employee retention as well as track and improve efficiencies and monitor change.

Access and integration of data is the lifeline of a machine learning system. With respect to predictive analysis services, predictions should be based on current reliable data. However, developing and managing data pipelines to feed a machine learning system is costly and complicated by the scalability of new data. Therefore, a need exists for improved computer apparatuses with a novel architecture for increased efficiency of operation, data collection, analysis, and machine learning.

SUMMARY

In one aspect, a computer network architecture with automated model pipeline and machine learning includes a prediction module with a prediction generator and an updated database, a learning module with a training submodule and the updated database, and a web application in electronic communication with both the prediction module and a user device. The learning module may be configured to receive a list of algorithm definitions and datasets, calibrate one or more defined algorithms with the database, test the calibrated algorithms with a plurality of evaluation metrics, store the calibrated algorithms and evaluation metrics in a library, select the best algorithm based on the best evaluation metrics, update further the database with third party data, and with user episode data, and re-execute the calibrate, test, store, and select steps after the update of the database step. The prediction generator may be configured to receive a user prediction request, including episode data and a client model, run the currently selected best algorithm corresponding to the user using the episode data, and generate prediction output, generate a prediction report based on the algorithm output, and transmit the prediction report to the user. The algorithm definitions may be of types that are members of the group comprising multi-level models, random forest regression, logistical regression, gamma-distributed regression, and linear regression; wherein, the third party data is from a party that is a member of the group comprising: hospitals, medical practices, insurance companies, credit reporting agencies, and credit rating agencies. The database may include patient medical data, patient personal data, patient outcome data, and medical treatment data. The episode data may include individual patient medical data and personal data. The user may be a member of the group comprising hospitals medical practices, and insurance companies. The user device may be remote from the prediction module, and the user device may be a member of the group comprising a computer, a desktop PC, a laptop PC, a smart phone, a tablet computer, and a personal wearable computing device. The web application may communicate with the user device by the Internet, or an extranet, or a VPN, or other network. The web application may be generic for any users, or customized for a specific user, or class of user. The web application may be specific to a specific class of user requests.

In another aspect, a computer network architecture with automated model pipeline and machine learning may include a prediction module with a prediction generator, an updated database, and a learning module with a training submodule and the updated database. The learning module may be configured to receive a list of algorithm definitions and datasets, calibrate one or more defined algorithms with the database, test the calibrated algorithms with a plurality of evaluation metrics, store the calibrated algorithms and evaluation metrics in a library, select the best algorithm based on the best evaluation metrics, update further the database with third party data, and with user episode data, and re-execute the calibrate, test, store, and select steps after the update of the database step.

In one embodiment, the prediction generator may be configured to receive a user prediction request, including episode data and a client model, run the currently selected best algorithm corresponding to the user using the episode data, and generate prediction output, generate a prediction report based on the algorithm output, and transmit the prediction report to the user.

In another embodiment, the algorithm definitions may be of types that are members of the group comprising multi-level models, random forest regression, logistical regression, gamma-distributed regression, and linear regression. The third party data may be from a party that is a member of the group comprising hospitals, medical practices, insurance companies, credit reporting agencies, and credit rating agencies. The database may include patient medical data, patient personal data, patient outcome data, and medical treatment data. The episode data may include individual patient medical data and personal data. The user may be a member of the group comprising hospitals medical practices, and insurance companies.

In still another embodiment, the computer architecture may include a web application in electronic communication with both the prediction module, and a user device.

In yet another embodiment, the user device is remote from the prediction module, and the user device is a member of the group comprising a computer, a desktop PC, a laptop PC, a smart phone, a tablet computer, and a personal wearable computing device.

In a further embodiment, the web application communicates with the user device by the Internet, or an extranet, or a VPN, or other network. The web application may be generic for any users, or customized for a specific user, or class of user. The web application may be specific to a specific class of user requests.

DESCRIPTION

Figure 1:
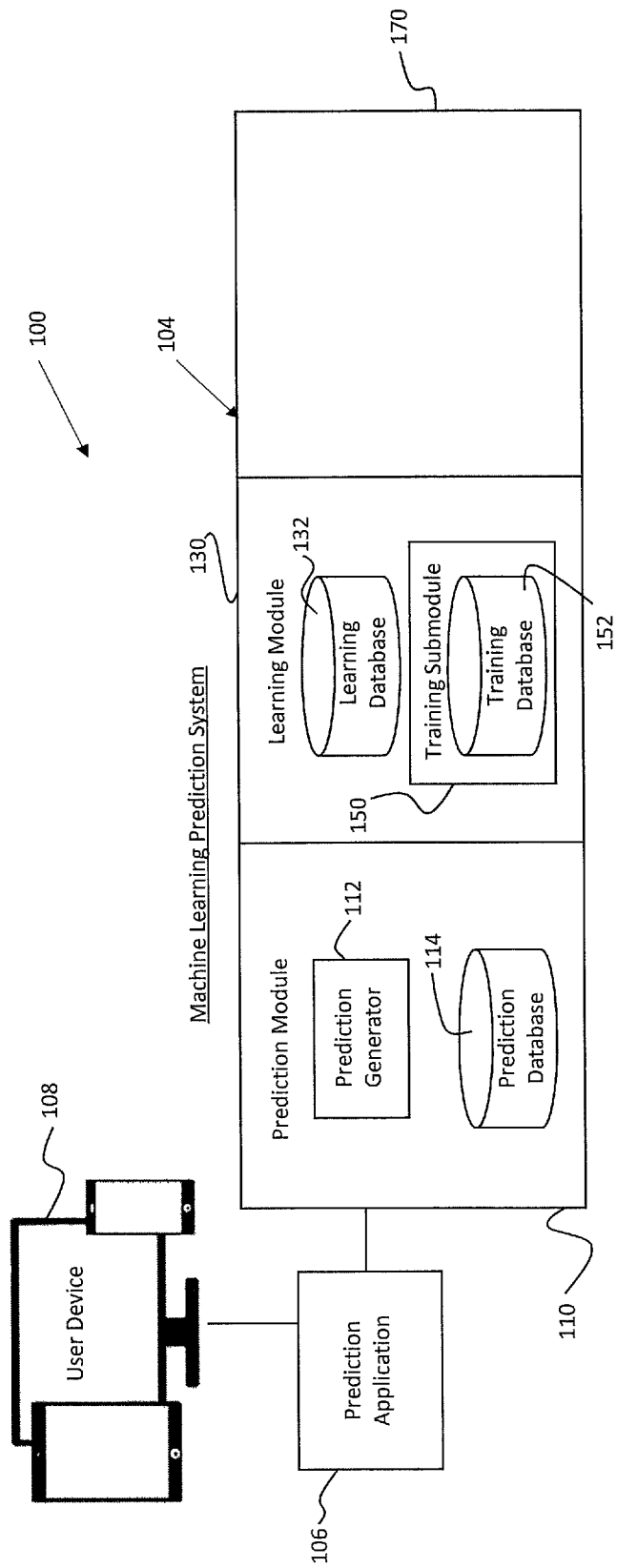
FIG. 1 schematically illustrates an overview of a computer network architecture including a machine learning prediction system according to various embodiments described herein.

The present disclosure describes a novel network architecture configured to produce and automatically improve predictive models, particularly for patient healthcare outcomes regarding for example, cost, quality and patient satisfaction. According to various embodiments, the network architecture allows automatic machine learning as new data sources are added, and new data is collected, and the predictive algorithms are recalibrated and reselected using the expanded, and hence more reliable, data. This architecture addresses, for example, new waste identification problems in healthcare without having to proportionally increase labor cost. The above may enable users of the architecture to quickly realize the value of new data.

Utilization of the novel architecture described herein may enable more efficient operation, hosting, maintenance, integration and use of new data and data sources, and continuous automatic improvement of predictive models by recalibration and reselection of algorithms based on the expanding data.

Machine learning may incorporate predictive model algorithms to execute predictive analytical operations. Learning may be supervised or unsupervised. In general, a predictive model analyzes historical data to identify patterns in the data. The patterns identified may include relationships between various events, characteristics, or other attributes of the data being analyzed. Modeling of such patterns may provide a predictive model whereby predictions may be made. Development of predictive models may employ mathematical or statistical modeling techniques such as curve fitting, smoothing, and regression analysis to fit or train the data. Such techniques may be used to model the distribution and relationships of the variables, e.g., how one or more events, characteristics, or circumstances (which may be referred to as "independent variables" or "predictor variables") relate to an event or outcome (which may be referred to as a "dependent variable" or "response").

A machine learning process may include developing a predictive model. For example, a dataset comprising observed data may be input into a modeling process for mapping of the variables within the data. The mapped data may be used to develop a predictive model. The machine learning process may also include utilizing the predictive model to make predictions regarding a specified outcome that is a dependent variable with respect to the predictive model. The machine may then be provided an input of one or more observed predictor variables upon which the output or response is requested. By executing the machine learning algorithm utilizing the input, the requested response may be generated and outputted. Thus, based on the presence or occurrence of a known predictor variable, the machine learning algorithm may be used to predict a related future event or the probability of the future event.

The present invention applies generally to predictive algorithms informed by data. When the data relates to medical patients and treatments, and the algorithms correlate patient data with treatments and healthcare outcomes, then the system produces a pipeline of predictive models for healthcare outcomes that constantly improve and evolve with the machine learning and artificial intelligence of the present invention. For clarity and economy of description, the terms machine learning and artificial intelligence are often used interchangeably herein.

Machine Learning and Artificial Intelligence Architecture

FIG. 1 provides a schematic overview of a flexible computer network architecture 100 according to various embodiments. The network architecture 100 may include a machine learning prediction system 104. The machine learning prediction system 104 may be configured to generate machine learning algorithms comprising predictive models, automatically select and calibrate predictive models, build databases containing multiple predictive models for multiple model types as well as metrics for each model, add new databases to the system, build existing databases integrating new data, update system predictive models utilizing new data, receive prediction requests, and generate output responses comprising predictions based on input parameters via execution of the machine learning algorithms. As described in more detail below, the machine learning prediction system 104 may include one or more local or distributed hardware units comprising servers, communication devices, data storage devices, and processors configured to execute instructions for performing the operations of the machine learning prediction system 104.

The network architecture 100 may also include one or more prediction applications 106. In some embodiments, the prediction application 106 includes one or more web applications. The prediction application 106 or web applications thereof may include or access episode request templates for defining prediction requests. Prediction applications 106 may be generic for any end user, semi-generic, or customized for a single end user.

In one embodiment, the web applications (i.e., prediction applications), the prediction module, and the learning module may reside in the cloud and be administered by the invention's operator. Web applications may be structured for specific users, classes of users, templates or related data and predictions. In the healthcare industry, web applications may seek prediction reports for outcomes of specific patient episodes, and focus on factors such as patient guidance, automated healthcare performance benchmarks, estimates of missing clinical episode costs related to incomplete health insurance claims, patient risk scoring, forecasting episode and annual costs, facilities rating systems adjusted for risk, and other points.

In a healthcare embodiment, when an end user provides a request for a prediction report, the end user may give specific patient data (e.g., patient metrics and treatment) to populate a selected episode profile or template in a selected web application. The user requests a prediction report, e.g., a prognosis (i.e., predicted outcomes). Other web applications may give other reports. e.g., possible treatments, probability of each possible result of each treatment choice, economics, and schedule of prognosis and treatment. The web application then automatically accesses the prediction module and transmits the episode data with the request, and receives back a prediction report from the prediction module.

Prediction applications 106 may be configured to interface one or more user devices 108 with the machine learning prediction system 104. The user device 108 may access or run the prediction application 106, which may be stored locally, remotely, or reside in the cloud. For example, the user device 108 may remotely access the prediction application 106 with a browser through a network connection, such as an Internet, extranet, or VPN connection. User devices 108 may include an electronic communication device such as a computer, laptop, PDA, tablet, wearable computing device, or smart phone. The user device 108 will typically function as an end point with respect to the network architecture 100 and interface users with the network architecture 100. Users may include customer or client end users, which may be in a commercial environment such as in a SaaS environment. In an example healthcare application, a user or user device 108 may be associated with a customer or customer grouping, which may be a specific hospital, doctor office, insurance company, or grouping of multiple hospitals, doctor offices, or insurance companies, for example.

The machine learning prediction system 104 may include a prediction module 110 and a learning module 130. The prediction module 110 may include a prediction generator 112 configured to process prediction requests and generate prediction responses with respect to specified outcomes. For example, prediction requests, which may also be referred to as report requests, may include episode data comprising observed data related to a response variable. Using the episode data, the prediction generator 112 may execute machine learning algorithms comprising prediction models stored in a prediction database 114.

The learning module 130 may be configured to execute computer learning tasks including generating, calibrating, updating and evaluating system prediction models. The learning module 130 may include a training submodule 150 configured to execute training functions, which may include executing training requests, to fit data comprising observed episode data to one or more model types defined in the machine learning prediction system 104

The machine learning prediction system 104 may include one or more databases, each of which may comprise one or more member databases, for storing episode data, metrics, model types, current best predictive models, archived predictive models, and other data from which the machine learning prediction system 104 may access to perform system operations. For example, the training submodule 150 may include a training database 152 that stores observed episode data for training system prediction models. The training database 152 may collect and accumulate data over time for use by the training submodule 150. In a healthcare application, for example, the training database 152 may include data relating to individual patients, episodes, and outcomes. In some embodiments, the training database 152 includes a customer's institutional data, which the training submodule 150 may access. In one embodiment, the customer's institutional data is restricted to us only for the customer. The training database 152 may also third party databases that may be used by the training submodule 150 to generate, update, or recalibrate system predictive models. Thus, the training submodule 150 may access or integrate third party databases. In some embodiments, the training database 152 includes one or more database repositories for medical data and socioeconomic data such as financial credit histories from credit rating companies. The training database 152 may reside in a single or multiple locations, be local or distributed, and may include third party databases accessible by the learning module 130 or training submodule 150. In one embodiment, the training database 152 may be divided or physical or logically partitioned into episode specific data libraries.

A library of system prediction models and associated metrics generated by the training submodule 150 may be stored in a learning database 132. The library may be used for evaluation of the archived models. For example, the learning database 132 may include multiple generated predictive models types of each of a plurality of specific episodes types. The learning module 130 may periodically or upon the occurrence of a predefined event, such as addition of new data or generation of new predictive models, compare metrics across the predictive models in the library to determine if a predictive model for a specific episode performs better than the predictive model for the episode that is stored in the prediction database 114, which the prediction module 110 currently uses for responding to prediction requests for the episode. If, based on the metrics comparison, the learning module 130 determines that another predictive model performs better than the one stored in the prediction database 114, the learning module 130 may replace the predictive model with the model determined to be the current best. The learning database 132 may maintain a record of the metrics and associated predicative models for future evaluations. In some embodiments, the learning module 130 may test or update the regression calibration of one or more algorithm to be used, and add episode data to the database to be kept and expanded and used by this and all subsequent queries.

In various embodiments, the network architecture 100 or machine learning prediction system 104 may also include an administration module 170. The administration module 170 may be configured to allow systems administrators to develop and control the machine learning prediction system 104, such as defining episode types. For example, system administrators may define patient episode types such as types of patient conditions to be handled, their metrics, and training databases 152 used. The machine learning prediction system 104 may be employed for machine learning and predictive analysis for any episode type. Episode types may include, for example, "hip and knee replacements under Medicare rules" or "pneumonia under Aetna Insurance" rules. The administration module 170 may provide, incorporate, or update episode type definitions, e.g., types of patients, metrics and parameters, and illness types. The administration module 170 may also allow system administrators to define which training database 152 or prediction database 114 each episode type will use. In some embodiments, system administrators may utilize the administration module 170 to add or integrate additional databases into the training databases 152, which may include third party databases. In the above or another embodiment, system administrators may utilize the administration module 170 to define which data each patient episode profile type will use. For example, utilizing the administration module 170, system administrators may define which parameters or attributes, such as predictor variables, associated with observed episode data is to be used for generating predictive models or predictions for specific episode types. An administrative application (see, e.g., FIG. 2) may also be used in addition to or instead of an administration module 170.

Further Network Architecture

Figure 2:
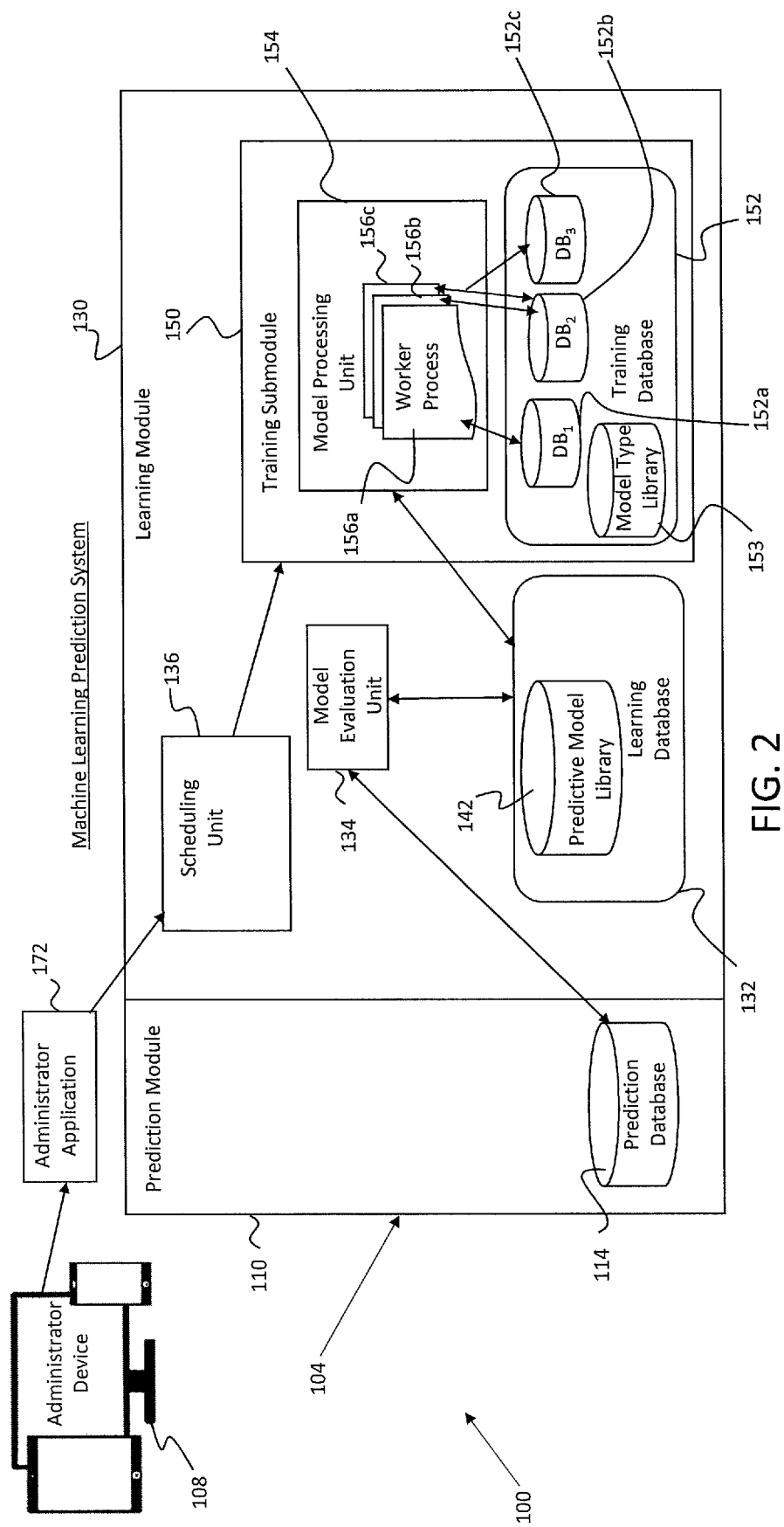
FIG. 2 schematically illustrates various aspects of a computer network architecture including a machine learning prediction system according to various embodiments described herein.

FIG. 2 illustrates an embodiment of the computer network architecture 100 and machine learning prediction module 104 performing a machine learning operation including one or more of training, evaluation, storage, or management of prediction functions. In particular, the learning module 130 may be configured to execute a machine learning process wherein episodes, such as clinical episodes, are built and continually updated in the learning and training databases 132, 152, which represent the confluence of program specific episode logic and actual care provided to large populations of patients.

As introduced above with respect to FIG. 1, the learning module 130 may include or access a training database 152, which may include episode specific data libraries 152a, 152b, 152c, from which a training submodule 150 may draw upon to generate or train system predictive models. In some embodiments, the training database 152 includes third party or customer specific databases. Operation of the training submodule 150 may utilize actual observed data in the training database 152 to generate predictive models and associated metrics for inclusion in a predictive model library 142 of the learning database 132. It will be appreciated that episode specific data libraries 152a, 152b, 152c may be distributed among multiple hardware and locations. For example, episode specific library 152a may be distributed on or among one or more hardware locations, which may include one or more third party databases or customer databases. Episode specific library 152b may similarly be distributed on or among one or more hardware locations, which may or may not include one or more hardware locations including episode specific library 152a.

The learning module 130 or training submodule 150 thereof may include a model type library. In the illustrated embodiment, the training database 152 includes a model type library 153. In various embodiments, model types (sometimes referred to as algorithms) may include one or more of multi-level models, random forest regression models, logistical regression models, gamma-distributed regression models, linear regression models, or combinations thereof. Other model types may be used. In one embodiment, the learning module 130 may be configured to expand utilization of additional model types or redefine or update current model types.

In various embodiments, the learning mode 130 may be configured to automatically, such as periodically or upon the occurrence of a system event, generate training requests. For example, system events may include addition of accessible episode data corresponding to specific episodes, such as addition of or updating of data in the training database 152. The learning module 130 may generate training requests that include all, multiple, or portions of one, more, or all datasets in an episode specific training database 152a, 152b, 152c. For example, the learning module 130 may include a scheduling unit 136 configured to automatically initiate a training process to test or update calibration of the predictive models. For example, training may be initiated with each query, number or volume of queries, periodically, upon introduction of new data, or other time period or event.

In some embodiments, system administrators may submit requests to the learning module 130 instead of or in addition to automatic request generation. In the illustrated embodiment, an administer device 109 interfaces with the scheduling unit 136 via an administrator application 172 to initiate the training process. The administrator device 109 may access or run the administrator application 172, which may be stored locally, remotely, or reside in the cloud. In one embodiment, the administrative application 172 comprises a web application remotely accessible by the administrator device via a browser through a network connection, such as an Internet, extranet, or VPN connection. The administrator device 109 may include an electronic communication device such as a terminal, computer, laptop, PDA, tablet, or smart phone. The training request initiated by the administrator device 109 via the administrator application 172 may include a request template providing a model definition and dataset.

The model definition may identify parameters and episode attributes to use for model fitting in the training process. The dataset may include observed episode data including attribute values of predictor variables and response variables. In some embodiments, the dataset provided in the request may identify all or a portion of episode data stored in the training database 152 for the episode type that corresponds to the model definition, which may be in addition to or instead of transmission of new data in the request.

As introduced above, the dataset may include observed episode attribute values from a plurality of episodes corresponding to the episode type indicated in the model definition. For example, the model definition may specify post-op knee replacement prognosis (Y) and identify attributes, e.g., age, weight, education, income, hospital location, procedure variation, or other attributes (X), to be used in the modeling. The dataset may then include a plurality of data points comprising episode attribute values $y_0, x_{01} \ldots, x_{0n}$ corresponding to the model definition. In various embodiments, multiple pairs of model definitions and datasets may be submitted to the training submodule 150, e.g., a list of requests comprising pairs of model definitions and datasets.

In various embodiments, the model definition may be generic to multiple types of models in the model type library 144. For example, the model definition may be applicable to two, more, or all types of models or category of types of models corresponding to an episode type. The model definition may directly or indirectly identify applicable model types. Alternatively or additionally, the learning module 130 may be configured such that model definitions are assumed to be applicable to all system model types unless indicated otherwise.

The training submodule 150 may include a model processing unit 154 configured to process training requests and generate predictive models according to the requests. The model processing unit 154 may employ one or more worker processes 156a, 156b, 156c to generate a fitted model, per the parameters of the request. Worker processes 156a, 156b, 156c may include modeling software programs, software functions, processes, or subroutines, for example. The model processing unit 154, or worker processes 156a, 156b, 156c thereof, may access the model type library 153 to obtain executable instructions for generating one or more predictive models for one or more of the model types using the dataset specified in the request.

In various embodiments, the model processing unit 154 may farm each model definition/dataset pair to a worker process 156a, 156b, 156c to generate fitted models. In one example of the training process, one or more worker process 156a, 156b, 156c may each be tasked with generating a fitted model, per the parameters of the request. As introduced above, the machine learning prediction system 104 may be configured to generically support multiple types of models. Accordingly, multiple fitted models may be generated corresponding to one or more model types. In some embodiments, each worker process 156a, 156b, 156c may run a script, such as a Python script, to generate respective fitted models. In one embodiment, worker processes 156a, 156b, 156c may access or be provided data specified in the request comprising one or more datasets or portions thereof from one or more specified episode specific training databases 152a, 152b, 152c. Alternately, worker processes 156a, 156b, 156c may be provided new or additional data identified by or included in the dataset of the training request. For example, the new or additional data may be accesses or obtained from a third party database. In some instances, all or a portion of the new or additional data may be retained and stored in the training database 152 and thereby expand available episode data for future fine tuning of the system's 104 episode modeling algorithms.

As introduced above, the model processing unit 154 may test generated predictive models, the metrics of which may be stored in the learning database 132. In the illustrated embodiment, the worker processes 156a, 156b, 156c test the fitted models generated from the episode definition/dataset pair in the request. The testing process may include one or more metric evaluations or other testing or evaluation schemes. In one example, worker processes 156a, 156b, 156c may perform k-fold cross-validation to estimate prediction ability of the generated fitted models. In a further example, k-fold cross-validation may include testing of a model via 5-fold cross-validation. K-fold cross-validation may include partitioning a dataset into k different partitions or folds. Fitting the model may therefore include training k−1 subsets as training data consistent with a model type and then testing the trained model with the remaining subset as a validation or test data. This may be repeated until all k subsets have been used as the validation or test data. Calculated cross-validation errors across the folds may be averaged. K-fold cross-validation may also be used to select the fitted model that is likely to be the most predictive with out-of-sample data.

The results of the model fitting and testing may be calculated by the model processing unit 154. For example, worker processes 156a, 156b, 156c may calculate evaluation metrics descriptive of the generated models, which may be used to compare models. Evaluation metrics may include, for example, one or more metrics selected from RMSE, mean bias, mean absolute error, area under the curve on a receiver operating characteristic plot, or combinations thereof. Other evaluation metrics may be used. For example, suitable evaluation metrics may be selected that correspond to the model task or design such as binary classification, multiclass, or multi-label (ROC, Cohen's Kappa, confusion matrix, MCC, accuracy classification score, F1 score, F-beta score, average Hamming loss, Jaccard similarly coefficient score). The results of the model fitting and testing may be captured in a learning database 132. The status of each model fitting worker process 156a, 156b, 156c may also be logged centrally, along with the status of the overall request process.

The learning module 130 may also include a model evaluation unit 134 configured to evaluate generated models in the predictive model library 142. For example, an RMSE, mean bias, mean absolute error, area under the curve on a receiver operating characteristic plot, and a date-time of model fit for each generated predictive model may be sent to the learning database 132 and stored in the predictive model library 142. The model evaluation unit 134 may use this captured test data to screen the predictive quality of the model versus captured test data of previous model versions applicable to a corresponding episode type, which may include comparisons across model versions within a model type or within multiple model types. If the model passes this screening, the model evaluation unit 134 may automatically incorporate the model into the prediction database 114 for use moving forward for future customer environments as the current best, or best-of-class, model for the corresponding episode type or possibly additional episode types.

The learning module 130 may be configured to periodically or upon occurrence of a predefined event test prediction accuracy of models in the predictive model library 142 against new, current, or existing episode data. For example, episode data may be dated in the training database to track currentness of the data to test ability of generated predictive algorithms to predict responses based on current episode data. Periodic prediction analysis may address drift, concept drift, or unintended honing or targeting of the model algorithm over time. Current or new episode data may also be obtained from a third party database or may be submitted in a request or imported into or associated with the training database 152, which may be an event that initiates analysis or evaluation of one or more system models, which may include best models, models that are not classified as current best models, or combinations thereof. A low calculated prediction accuracy may initiate retraining, updating, recalibration, or replacement of a current best model with a better performing model from the predictive model library 142 or a newly generated model fit and tested as above from new or existing episode data.

Accordingly, the machine learning prediction system 104 may be configured for machine learning and artificial intelligence during actual use by constant automatic fine-tuning of the calibration of the algorithm and expansion of the databases. The learning module 130 may test or update the regression calibration of system algorithms in the prediction database 114 and predictive model library 142 and add episode data to the training database 152 to be kept and expanded and used by subsequent queries.

Machine Learning Architecture

Figure 3:
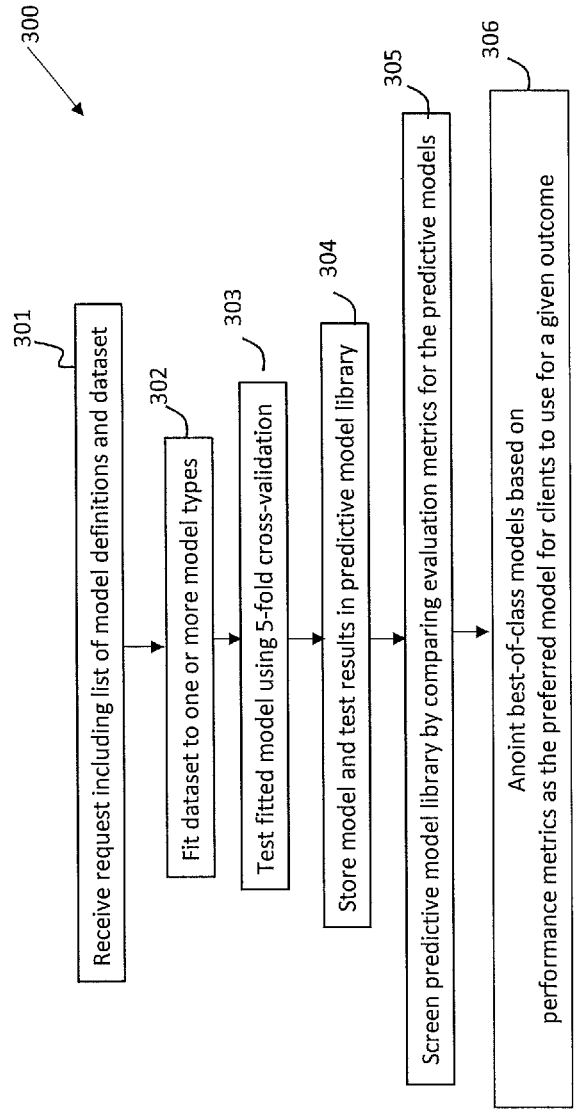
FIG. 3 is a prediction process of a computer network architecture including a machine learning prediction system according to various embodiments described herein.

FIG. 3 illustrates a training process 300 that may be utilized by the machine learning prediction system 104 (see, e.g., FIGS. 1 & 2) according to various embodiments. The training process 300 may include receiving a user request that includes a list of model definitions and a dataset 301, which may be similar to the request described with respect to FIG. 2. The dataset may then be fitted to one or more model types 302. For example, the training submodule may fit the dataset to one or more models types, that is, a plurality of predictive model algorithms may be calibrated by the available data set. The model types, or predictive algorithms, may include multi-level models, random forest regression models, logistical regression models, gamma-distributed regression models, linear regression models, combinations thereof, or other types. The fitted models (i.e., calibrated algorithms) may then be tested by a 5-fold cross-validation 303, although, in some embodiments, the fitted model may be tested using other testing techniques. The models and the test results may be stored in the predictive model library 304. The test results may include, for example, one or more of five cross-validation evaluation metrics selected from RMSE (root means square error), mean bias, mean absolute error, area under the curve on a receiver operating characteristic plot, or date-time of model fit. The models in the predictive model library, which may include models currently being used by the prediction module for servicing client requests, may be screened by comparing the evaluation metrics 305. Next, the screening results may be used to identify the best current model for a given response (that is, the algorithm with the best evaluation metrics after calibration with the current data is the best current algorithm), and that model may be anointed best-of-class model based on the performance metrics, that is, the preferred model for clients to use for a given outcome 306. Thus, if the screen indicates that a predictive model in the prediction model library performs better than a model currently being used by the prediction module for servicing the customer requests, the newly anointed best-of-class model may replace that model as the model used by the prediction module for servicing the customer request for the corresponding given response outcome.

The data used to calibrate, evaluate and select the algorithms (i.e., the models) is constantly updated by addition of applicable databases from users, and from third-party vendors, such as hospitals, medical practices, insurance companies, credit scoring agencies, and credit history agencies. Also, the data available is updated by the data from each user request for an individual prediction for a patient episode. The accumulating data continually expands over time and shall become an increasingly valuable asset. The training module may be automatically rerun periodically, occasionally, or with each individual user request for an individual prediction. That is, the algorithms may be automatically recalibrated, re-evaluated and reselected periodically, occasionally, or otherwise, using the then current expanding database. More data is more statistically reliable, so automatically re-running of the training module with more data makes the model predictions increasingly better, that is, this machine learning is improving the prediction results. This provides an automatic artificial intelligence pipeline of ever-improving predictive models.

Network Architecture with Web Applications

Figure 4:
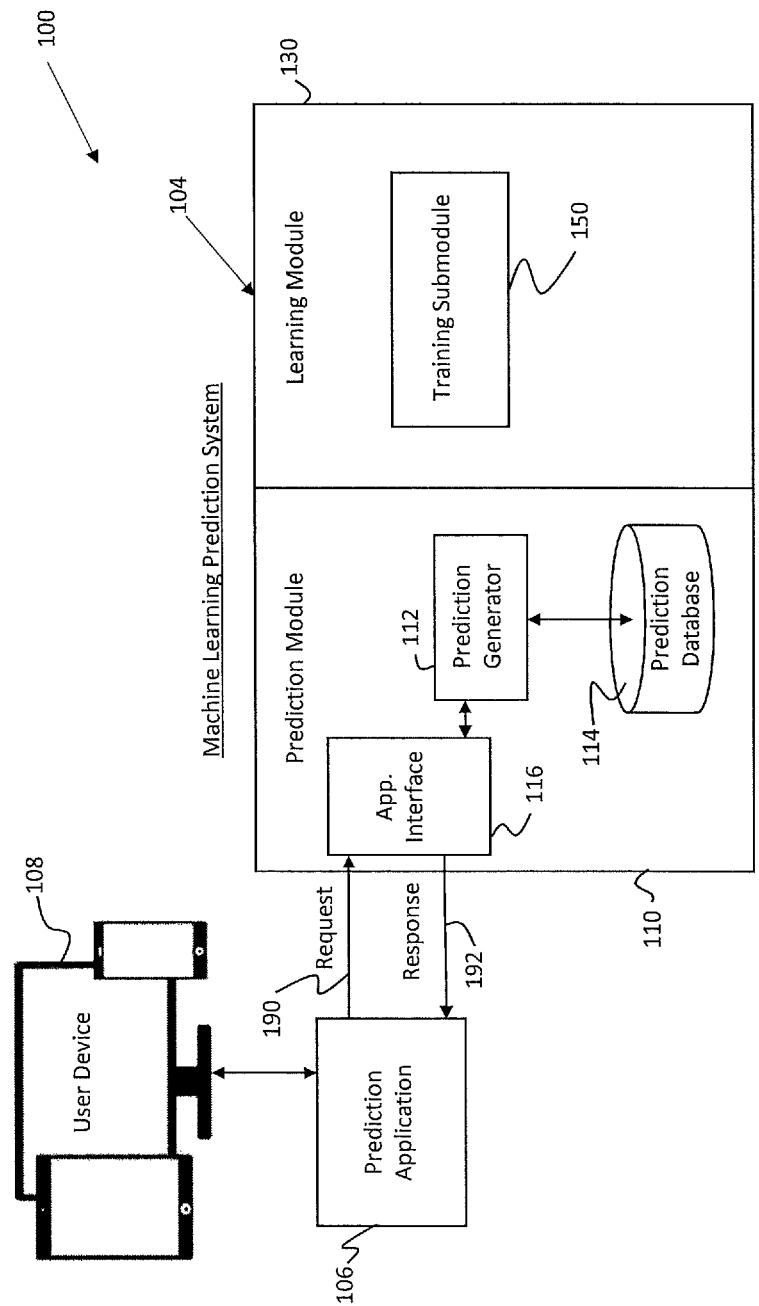
FIG. 4 schematically illustrates various aspects of a computer network architecture including a machine learning prediction system according to various embodiments described herein.

FIG. 4 illustrates operation of the prediction module 110 with respect to processing a prediction request according to various embodiments. An end user may access the machine learning system 104 with a user device 108 via a prediction application 106 (a web application) and request a report. In the request, the end user may provide specific episode data, e.g., specific patient data (patient metrics and treatment), to populate a selected episode profile or template in a selected web application associated with the prediction application 106. The web application may be specific to the request report, e.g., a response such as a prognosis or predicted outcome based on the provided episode data. The prediction application 106 may include other web applications that may provide other reports, e.g., possible treatments, probability of each possible result of each choice, economics, or schedule of prognosis and treatment. The web application may then automatically access the machine learning prediction system 104 and transmit the episode data with the request, as indicated by arrow 190. The prediction module 110 may include an application interface 116 configured to handle communication between the prediction application 106 and the prediction module 110.

The request may be provide to a prediction generator 112 to generate the requested response. Using the desired response specified in the report request and available episode data, the prediction generator 112 selects the appropriate model in the prediction database 114. An identified client model may also be used. The prediction generator 112 may then execute the selected model utilizing the episode data specified in the request to generate a prediction response for the specified outcome in the request. The prediction module 110 may then provide the requested report including the prediction response, indicated by arrow 192, to the prediction application 106, via the application interface 116, for presentation to the user with the user device 108.

Prediction Architecture

Figure 5:
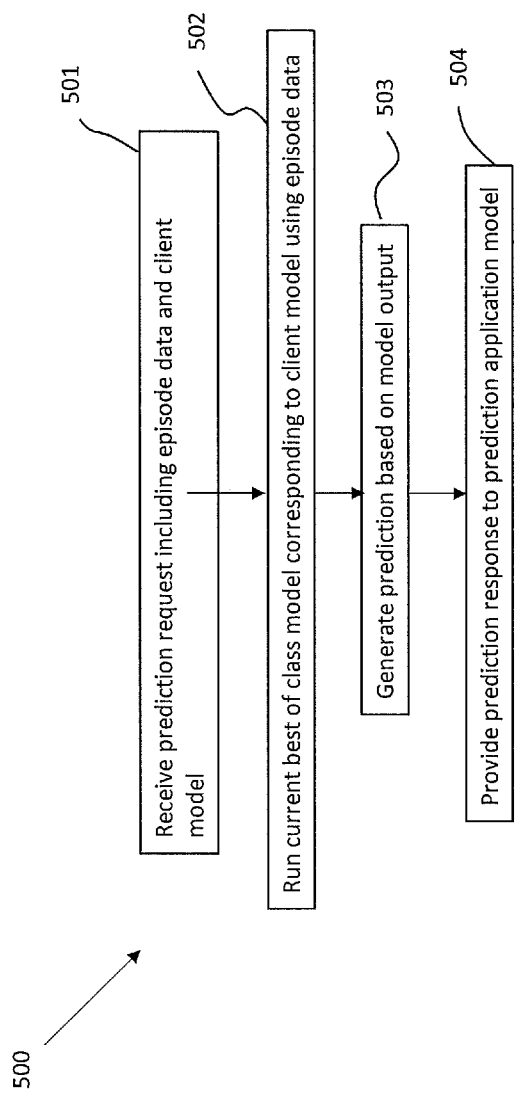
FIG. 5 is a training process of a machine learning prediction system according to various embodiments described herein.

FIG. 5 illustrates a prediction process 500 that may be utilized by the machine learning prediction system 104 (see, e.g., FIGS. 1, 2, & 4) according to various embodiments. The process 500 includes receiving a prediction request 501. As described above with respect to FIG. 4, the prediction request may include a request for a report and include specific episode data and identify a client model. Using the episode data and best in class model in the prediction database corresponding to the client model, the episode data may be input into the model and model may be run 502. The running of the model with the episode data generates a prediction response based on the model output 503. The prediction response may then be provided to the client requester 504, e.g., the prediction module may transmit the response to the prediction application for display, storage, or routing to the user device or another location specified by the client user or request.

Further Machine Learning Architecture

Figure 6:
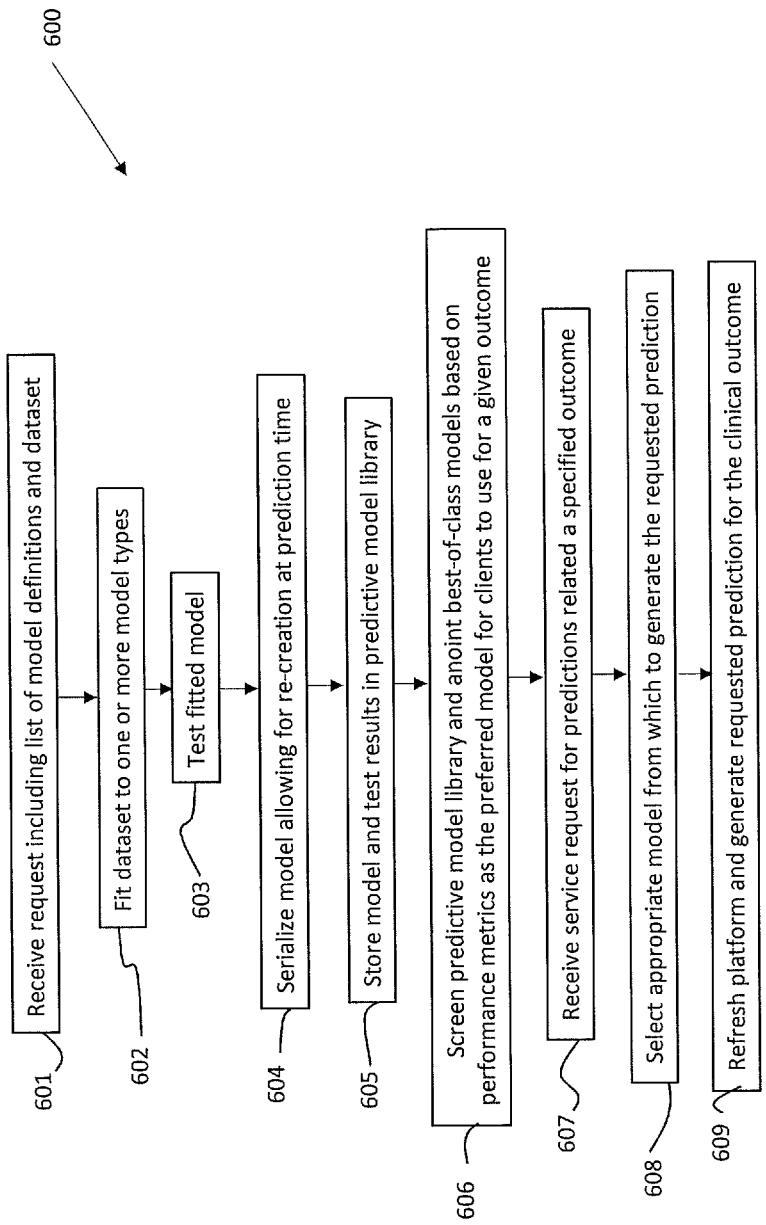
FIG. 6 is a training and prediction process of a computer network architecture including a machine learning prediction system according to various embodiments described herein.

FIG. 6 illustrates a training and prediction process 600 that may be utilized by the machine learning prediction system 104 (see, e.g., FIGS. 1, 2, & 4), according to various embodiments. The process 600 may include receiving a request including a list of model definitions and a dataset 601. The request may be automatically generated, submitted by a system administrator similar to FIG. 2, or submitted by a customer user. The model definition may include identifying data, parameters, or criteria for a modeling protocol. For example, the request may specify a training dataset, outcomes to model, and factors that should be used to power the model. The dataset may then be fit to one or more model types, which may include multiple models corresponding to a single model type, based on the model definitions 602. The fitted model may then be tested, which may include estimating in and out of sample error 603. As described with respect to FIG. 2, testing may include cross-validation such as k-fold cross-validation (e.g., 5-fold cross-validation). Following testing, the model may be serialize or otherwise summarized in a way that allows for re-creation at prediction time 604. The model and test results may be stored in the predictive model library 605. The process may further include screening the predictive model library and anointing best-of-class models based on performance metrics as the preferred model for clients to use for a given prediction response request 606.

The process may further include receiving service requests for predictions relating to a specified clinical outcome 607. Next, cased on the client request, a selection of the appropriate model from which to generate the requested prediction response may be made 608. With the appropriate model selected, the next step may include refresh/generate requested predictions for the clinical outcomes 609.

Components of an Architecture

Figure 7:
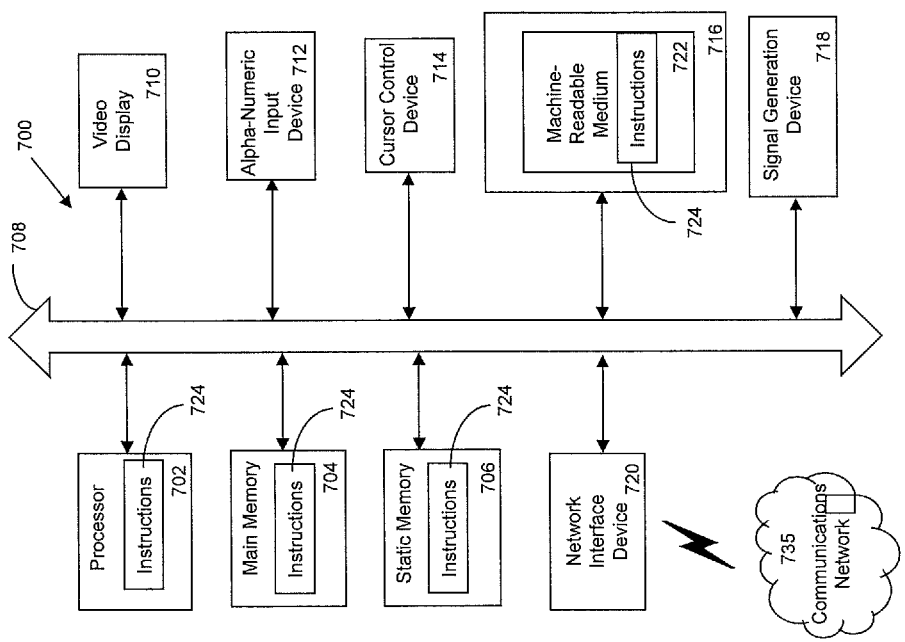
FIG. 7 schematically illustrates components of a system according to various embodiments described herein.

Referring to FIG. 7, at least a portion of the present invention may incorporate one or more computer apparatuses 700. Such a computer apparatus 700 may comprise a machine such as, but not limited to, a computer system, apparatus, or other arrangement of one or more computing devices within which a set of instructions 724, when executed, may cause the machine to perform any one or more of the methodologies or functions discussed above alone or in conjunction other one or more additional machines associated with the network or system, e.g., network architecture 100 or machine learning prediction system 104 described herein, or another network or system. While a single machine 701 is illustrated in FIG. 7, the term "machine" shall also be taken to include any collection of machines that individually or jointly execute a set (or multiple sets) of instructions 724 to perform any one or more of the methodologies discussed herein. The machine may be configured to facilitate various operations conducted by the system. For example, the machine may be configured to, but is not limited to, assist the network or system by providing processing power to assist with processing loads experienced in the network or system, by providing storage capacity for storing instructions 724 or data traversing the network system, or by assisting with any other operations conducted by or within the network or system.

In some embodiments, the computer apparatus 700 or a machine thereof may operate as a standalone device. In some embodiments, the computer apparatus 700 or a machine 701 thereof may be connected via a communication network 735 to and assist with operations performed by other apparatuses, machines, or systems. For example, the computer apparatus 700 or a machine 701 thereof may be connected with any component in the network or system. In a networked deployment, the computer apparatus 700 or a machine thereof may operate in the capacity of a server, server stack, or a client, such as a client user machine, in a server-client user network environment, or as a peer machine in a peer-to-peer (or distributed) network environment. The computer apparatus 701 or a machine thereof may comprise a server computer, a client user computer, a personal computer (PC), a tablet PC, a laptop computer, a desktop computer, a control system, a network router, switch or bridge, or any machine capable of executing a set of instructions 724 (sequential or otherwise) that specify actions to be taken by that computer apparatus 700 or a machine 701 thereof. In one example, the computer apparatus 700 comprising one or more machines 701 is arranged to have a distributed architecture employing a suitable model such as a client-server model. In one embodiment, the computer apparatus 700 may include a web service, e.g., service oriented architecture (SOA) or simple object access protocol (SOAP). The computer apparatus 700 may include a software as a service (SaaS) platform. The computer apparatus 700 may include representational state transfer style resources or resource oriented architecture (ROA). The computer apparatus 700 may include one or more processors, servers, databases, networks or network devices, and peripherals configured to obtain and transmit data and initiate operations configured to perform in whole or in part the operations of the system or platform thereof.

The computer apparatus 700 may include a processor 702, e.g., a central processing unit (CPU), a graphics processing unit (GPU, or both), a main memory 704 and a static memory 706, which communicate with each other via a bus 708. The computer apparatus 700 may further include a video display unit 710, which may be, but is not limited to, a liquid crystal display (LCD), a flat panel, a solid state display, or a cathode ray tube (CRT). The computer apparatus 700 may include an input device 712, such as, but not limited to, a keyboard, a cursor control device 714, such as, but not limited to, a mouse, a disk drive unit 716, a signal generation device 718, such as, but not limited to, a speaker or remote control, and a network interface device 720.

The disk drive unit 716 may include a machine-readable medium 722 on which is stored one or more sets of instructions 724, such as, but not limited to, software embodying any one or more of the methodologies or functions described herein, including those methods illustrated above. For example, the learning or training submodule 130, 150 described herein may include messaging or queuing processes or functions. Thus, the learning or training submodule may include Kue library to handle task distribution and coordination between worker process submodules, which may be backed by Redis in-memory key-value store with pub/sub. The instructions 724 may also reside, completely or at least partially, within the main memory 704, the static memory 706, or within the processor 702, or a combination thereof, during execution thereof by the computer system 700. The main memory 704 and the processor 702 also may constitute machine-readable media.

Other Matters

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example network or system is applicable to software, firmware, and hardware implementations.

In accordance with various embodiments of the present disclosure, the processes described herein are intended for operation as software programs running on a computer processor. Furthermore, software implementations can include, but are not limited to, distributed processing or component/object distributed processing, parallel processing, or virtual machine processing that may be constructed to implement the methods described herein.

The present disclosure describes various modules, which may also be referred to as sub-modules, generators, engines, systems, subsystems, components, units, and the like. Such modules may include functionally related hardware, instructions, firmware, or software. Modules may include physical or logical grouping of functionally related applications, services, resources, assets, systems, programs, databases, or the like. Modules or hardware storing instructions or configured to execute functionalities of the modules may be physically located in one or more physical locations. For example, modules may be distributed across one or more networks, systems, devices, or combination thereof. It will be appreciated that the various functionalities of these features may be modular, distributed, and/or integrated over one or more physical devices. While the learning database as well as the training databases are illustrated individually as discrete elements, it will be appreciated that such logical partitions may not correspond to physical partitions of the data. For example, all or portions of the databases may reside or be distributed among one or more hardware locations. Further, while screening for best-of-class or current best model is generally described as including scanning the predictive model library 142, this library 142 includes the models currently used by the prediction module 110, references to such models, evaluation metrics related to such data, or other data from which the screening may be performed to properly screen the library 142 of predictive models for the best-of-class or current best model.

The present disclosure contemplates a machine-readable medium 722 containing instructions 724 so that a device connected to the communications network 735, another network, or a combination thereof, can send or receive voice, video or data, and to communicate over the communications network 735, another network, or a combination thereof, using the instructions. The instructions 724 may further be transmitted or received over the communications network 735, another network, or a combination thereof, via the network interface device 720.

While the machine-readable medium 722 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of the network architecture, systems, and processes that might make use of the structures described herein. While the present disclosure generally describes the inventive network architecture, systems, and process with respect to healthcare applications, the healthcare field is but only one of many potential applications. Indeed, those having skill in the art will appreciate that the network architecture, systems, and processes described herein may find application in many industries. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

What is claimed is:

1. A computer network architecture with automated model pipeline artificial intelligence, and machine learning, comprising:

a prediction module with a prediction generator and a prediction database, and a learning module with a learning database and a training database, the learning database including a predictive model library storing calibrated algorithms and associated evaluation metrics, and the training database including a model type library storing algorithms for a plurality of model types, and a web application in electronic communication with both the prediction module and a user device;

wherein, the learning module is configured to:
 receive a list of algorithm definitions and a dataset,
 calibrate one or more algorithms for a plurality of the model types with the dataset,
 test the calibrated algorithms with a plurality of evaluation metrics,
 store the calibrated algorithms and evaluation metrics in the predictive model library,
 select an algorithm from the calibrated algorithms based on the evaluation metrics and store the selected algorithms in the prediction database,
 update the training database with third party data, and user episode data, and
 re-execute the calibrate, test, store, select, and update steps automatically and continually, either periodically, occasionally, or with each user prediction request;

wherein, the prediction generator is configured to:
 receive the user prediction request, including episode data and a client model,
 update the training database with the episode data in the user prediction request,
 run the currently selected algorithm corresponding to the user using the episode data, and generate prediction output,
 generate a prediction report based on the algorithm output, and
 transmit the prediction report to the user;

wherein the specified prediction output includes a plurality of the specified healthcare outcomes with at least one output for each of: patient healthcare outcomes, costs, quality of care, patient satisfaction, insurance claims, and clinical outcomes;

wherein, the model types include at least one of each of:
 multi-level models,
 random forest regression,
 logistical regression,
 gamma-distributed regression, and
 linear regression;

wherein, the third-party data is from a plurality of parties, with at least one party of each type in the group of types comprising:
 hospitals,
 medical practices, insurance companies,
credit reporting agencies, and
credit rating agencies;
wherein, the training database includes patient medical data, patient personal data, patient outcome data, and medical treatment data;
wherein, the episode data includes individual patient medical data and personal data; and
wherein, the user is a member of the group comprising:
hospitals
medical practices, and
insurance companies;
wherein, the user device is remote from the prediction module, and the user device is a member of the group comprising:
a computer,
a desktop PC,
a laptop PC,
a smart phone,
a tablet computer, and
a personal wearable computing device;
wherein, the web application communicates with the user device by the Internet, or an extranet, or a VPN, or other network, and the web application is generic for any users, or customized for a specific user, or class of user, and
wherein, the web application is specific to a specific class of user requests, and
wherein, the prediction generator is further configured to:
receive a user prediction request for specified healthcare outcomes, including episode data and a client model,
run the currently selected algorithm corresponding to the user using the episode data, and generate prediction output for the specified healthcare outcomes,
generate a prediction report for the specified healthcare outcomes based on the algorithm output, and
transmit the prediction report to the user.

2. A computer network architecture with automated model pipeline artificial intelligence, and machine learning, comprising:
a prediction module with a prediction generator and a prediction database, and
a learning module with a learning database and a training database, the learning database including a predictive model library storing calibrated algorithms and associated evaluation metrics, and the training database including a model type library storing algorithms for a plurality of model types,
wherein, the learning module is configured to:
receive a list of algorithm definitions and a dataset,
calibrate one or more algorithms for a plurality of the model types with the dataset,
test the calibrated algorithms with a plurality of evaluation metrics,
store the calibrated algorithms and evaluation metrics in the predictive model library,
select an algorithm from the calibrated algorithms based on the evaluation metrics and store the selected algorithm in the prediction database,
update the training database with third party data, and user episode data, and
re-execute the calibrate, test, store, select, and update steps automatically and continually, either periodically, occasionally, or with each user prediction request;
wherein, the prediction generator is configured to:
receive the user prediction request, including episode data and a client model,
update the training database with the episode data in the user prediction request,
run the currently selected algorithm corresponding to the user using the episode data, and generate prediction output for the specified healthcare outcomes,
generate a prediction report for the specified healthcare outcomes based on the algorithm output, and
transmit the prediction report to the user.

3. The computer network architecture of claim 2, wherein the specified prediction output includes a plurality of the specified healthcare outcomes with at least one output for each of: patient healthcare outcomes, costs, quality of care, patient satisfaction, insurance claims, and clinical outcomes.

4. The computer network architecture of claim 2, wherein:
the model types include at least one of each of:
multi-level models,
random forest regression,
logistical regression,
gamma-distributed regression, and
linear regression;
the third-party data is from a plurality of parties, with at least one party of each type in the group of types comprising:
hospitals,
medical practices,
insurance companies,
credit reporting agencies, and
credit rating agencies;
the training database includes patient medical data, patient personal data, patient outcome data, and medical treatment data;
the episode data includes individual patient medical data and personal data; and
the user is a member of the group comprising:
hospitals
medical practices, and
insurance companies.

5. The computer network architecture of claim 2, further comprising:
a web application in electronic communication with both the prediction module, and a user device.

6. The computer network architecture of claim 5, wherein the user device is remote from the prediction module, and the user device is a member of the group comprising:
a computer,
a desktop PC,
a laptop PC,
a smart phone,
a tablet computer, and
a personal wearable computing device.

7. The computer network architecture of claim 5, wherein the web application communicates with the user device by the Internet, or an extranet, or a VPN, or other network, and the web application is generic for any users, or customized for a specific user, or class of user, and
wherein, the web application is specific to a specific class of user requests.

* * * * *